United States Patent [19]

Michaelis et al.

[11] 4,305,867
[45] Dec. 15, 1981

[54] NOVEL ORGANOTIN COMPOUNDS

[75] Inventors: Klaus-Peter Michaelis, Lindenfels; Horst Müller, Fürth, both of Fed. Rep. of Germany

[73] Assignee: Ciba-Geigy Corporation, Ardsley, N.Y.

[21] Appl. No.: 99,951

[22] Filed: Dec. 3, 1979

[30] Foreign Application Priority Data

Dec. 8, 1978 [CH] Switzerland ............... 12555/78

[51] Int. Cl.³ .................. C08K 5/56; C08K 5/57; C07F 7/22
[52] U.S. Cl. ..................... 260/45.75 S; 260/410.6; 260/429.7
[58] Field of Search ............ 260/429.7, 410.6, 45.75 S

[56] References Cited

U.S. PATENT DOCUMENTS

| | | | |
|---|---|---|---|
| 2,641,588 | 6/1953 | Leistner et al. | 260/45.75 S |
| 2,790,785 | 4/1957 | Ramsden et al. | 260/429.7 X |
| 2,870,182 | 1/1959 | Leistner et al. | 260/429.7 |
| 3,931,263 | 1/1976 | Molt | 260/429.7 |
| 4,058,543 | 11/1977 | Mack | 260/45.75 S |
| 4,104,292 | 8/1978 | Dworkin | 260/410.6 X |
| 4,193,913 | 3/1980 | Abeler | 260/429.7 X |

OTHER PUBLICATIONS

Sawyer Organotin Compounds, Marcel Dekker, Inc., N.Y., v. 2, p. 181 (1971).

*Primary Examiner*—Helen M. S. Sneed
*Attorney, Agent, or Firm*—Harry Falber

[57] ABSTRACT

Organotin compounds of the formula I

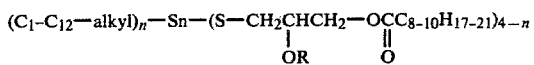

(I)

wherein n is 1 or 2, and R is a $C_1$–$C_{18}$-acyl group, as stabilizers for halogen-containing polymers.

7 Claims, No Drawings

NOVEL ORGANOTIN COMPOUNDS

The invention relates to novel organotin compounds, to their production, to their use as stabilisers for halogen-containing polymers, and to the polymers which are stabilised therewith.

From the German Offenlegungsschrift No. 2,531,308 are known mono- or di-organotin mercaptohydroxyalkylcarboxylic acid ester monosulfides, for instance from Example 10 is known monomethyltin-tris-(monothioglycerol diacetate, which compounds can be used for stabilising polyvinyl chloride and other halogen-containing polymers.

In practical application, these known organotin stabilisers are however not always satisfactory, particularly with regard to freedom from smell, to processing characteristics at elevated temperature and to thermal stability, and also in the case of special processes, for example when the stabilisers are used in tube production.

It was the object of the present invention to avoid these disadvantages of the compounds of the prior art, and to provide stabilisers which do not have the said disadvantages or have them to a lesser extent.

Accordingly, the invention relates to organotin compounds of the formula I

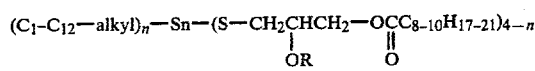

wherein n is 1 or 2, and R is a $C_1$–$C_{18}$-acyl group.

In the compounds of the formula I, n can be 1 or 2, so that mono- and di-alkyl-tin compounds are meant, which can also occur as mixtures. Preferably however n is 1.

The radical —C(=O)$C_{8-10}H_{17-21}$ represents a mixture of —C(=O)$C_8H_{17}$ and —C(=O)$C_{10}H_{21}$, which mixture is obtainable commercially; the radical can however also embrace all the individual meanings.

As $C_1$–$C_{18}$-acyl, the radical R is preferably $C_1$–$C_{18}$-alkanoyl, $C_7$–$C_{11}$-aroyl or $C_4$–$C_{18}$-alkoxycarbonylalkanoyl, such as benzoyl, tert-butylbenzoyl, a ($C_1$–$C_8$-alkyl)-maleic acid half-ester, such as methylmaleic acid half-ester, or in particular acetyl or propionyl. Acyl R is however equally preferably also acetoacetyl.

The alkyl groups bound to the tin are preferably straight-chain, and are particularly methyl, n-butyl or n-octyl.

Preferred compounds of the formula I are therefore those wherein n is 1 or 2, and R is $C_1$–$C_{18}$-alkanoyl or acetoacetyl.

Particularly preferred are compounds of the formula I wherein n is 1, and R is acetyl, propionyl or acetoacetyl.

More especially preferred are compounds of the formula I wherein the alkyl group bound to the tin is methyl, n-butyl or n-octyl, n is 1, and R is acetyl, propionyl or acetoacetyl; and also the compounds given in the Examples, as well as n-$C_8H_{17}$Sn[SCH$_2$CH(OCOCH$_3$)CH$_2$—O—COC$_{10}$H$_{21}$]$_3$ and n-$C_8H_{17}$Sn[SCH$_2$CH(OCOCH$_2$COCH$_3$)CH$_2$—O—COC$_{10}$H$_{21}$]$_3$.

The compounds of the formula I can be produced by methods known per se; they can thus be obtained by the processes described in the German Offenlegungsschrift No. 2,531,308, for example by reacting a tin halide of the formula ($C_1$–$C_{12}$-alkyl)$_n$—SnHal$_{4-n}$ with a monothioglycerol diester of the formula II

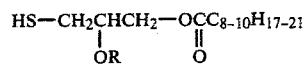

wherein R has the meaning defined in the foregoing. The reaction is performed preferably in a solvent, especially in a two-phase solvent, such as a water/organic solvent, for example water/alkane, such as water/heptane, advantageously in the presence of a buffer, such as sodium bicarbonate, and at slightly elevated temperature, such as at 30°–60° C. Advantageously, 1 mol of tin trihalide is reacted with 3 mols of the ester of the formula II, or 1 mol of tin dihalide with 2 mols of the ester of the formula II. It is however also possible to replace the tin halide, either completely or partially, by a corresponding tin oxide, and to obtain, depending on the employed amount thereof, so-called superbasic tin compounds, which likewise form subject matter of the invention.

The esters of the formula II are novel and likewise are subject matter of the present invention. The symbol R therein has the generally preferred meanings given above, and is in particular acetyl or propionyl. These esters are suitable for use in the process according to the invention for producing compounds of the formula I.

The stabilisers according to the invention are excellently suitable for protecting chlorine-containing thermoplasts against degradation caused by the action of heat and light. The amounts of the respective compounds of the formula I incorporated into the plastics material are in general 0.01 to 10 percent by weight, preferably 0.1 to 5 percent by weight. Further subject matter of the present invention is thus constituted by thermoplastic moulding compounds containing 0.01 to 10 percent by weight, relative to the thermoplastic mixture, of a stabiliser of the formula I.

The following may be mentioned as examples of chlorine-containing thermoplasts: polyvinylidene chloride, post-chlorinated polyolefins, and preferably polymers formed from or based on vinyl chloride. Suitable such polymers are E-, S- and M-PVC, and the polyvinyl chloride can also contain plasticisers and be post-chlorinated. Particularly preferred however is hard PVC, from which can be produced for example finished parts for external application, using known processes, such as injection moulding and extrusion.

Comonomers for thermoplasts based on vinyl chloride which may be mentioned are: vinylidene chloride, trans-dichloroethane, ethylene, propylene, butylene, maleic acid, acrylic acid, fumaric acid, itaconic acid or vinyl acetate.

It is possible to incorporate, before, during or after addition of the stabiliser according to the invention, depending on the purpose of application of the moulding compound, further additives, such as further stabilisers, lubricants, preferably montan waxes or glycerol esters, fillers, reinforcing fillers, such as glass fibres, and modifiers, for instance additives improving impact strength.

The following Examples further illustrate the invention. Parts and percentages relate to weight.

EXAMPLE 1

2.5 g of sodium hydrogen sulfide is added to 250 ml of methanol, and the solution is saturated at 25° C. with hydrogen sulfide. There is subsequently added dropwise, within 2 hours, 228 g of "CARDURA-E-10" epoxide

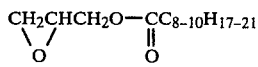

during which time hydrogen sulfide is continuously fed in in the amount which the reaction mixture can just absorb. The temperature must not exceed 25°–30° C., in order to prevent the formation of corresponding thioethers.

The catalyst is washed with a small amount of dilute sulfuric acid; the reaction mixture is then extracted with ether, and the solvent is removed in vacuo. There is thus obtained the monothioglycerol ester, $HSCH_2CH(OH)CH_2$—O—$COC_{8-10}H_{17-21}$, which can be directly further used.

EXAMPLE 2

260 g of the monothioglycerol ester described in Example 1 is diluted with 145 g of acetic anhydride. To this solution is added dropwise, with ice-water cooling, 15 ml of concentrated sulfuric acid. The temperature should not exceed 40° C. After being stirred for one hour, the reaction mixture is diluted with water and extracted with ether; the ether is washed neutral with saturated sodium hydrogen carbonate solution to obtain the mercapto diester $HSCH_2CH(OCOCH_3)CH_2$—O—$COC_{8-10}H_{17-21}$, as a completely odourless oil, after distillation at 130° C./0.1 Torr, having an SH content of 10.2%.

EXAMPLE 3

130 g of propionic anhydride is added to 260 g of mercaptoglycerol monoester from Example 1, and to this solution is added dropwise, with ice-water cooling, 20 ml of concentrated sulfuric acid. The temperature should not exceed 40° C. The reaction mixture is stirred for 1 hour; it is then diluted with water and extracted with ether; the ether phase is washed neutral with saturated sodium hydrogen carbonate solution to obtain the mercapto diester of the formula $HSCH_2CH(OCOCH_2CH_3)CH_2$—O—$COC_{8-10}H_{17-21}$ as a completely odourless oil; SH content 9.4%.

EXAMPLE 4

150 ml of acetoacetic acid ethyl ester is added to 52.4 g of mercaptoglycerol monoester from Example 1, and the mixture is heated until a total of 10 ml of ethanol distills off. After cooling, the excess acetoacetic acid ethyl ester is evaporated off in vacuo to obtain, in quantitative yield, the acetoacetylated mercaptoglycerol ester as a colourless and odourless compound having an SH content of 9.3%.

EXAMPLE 5

To 700 g of the mercapto diester of Example 2 having a mercapto content of 9.2% is added 155.3 g of mono-n-butyltin oxide (MBTO) having a total tin content of 50.6% Sn, the monotin content being 48.0%, and the mixture is heated to about 80° C. with stirring, and the formed reaction water is removed in vacuo. After cooling, the reaction product is filtered clear of the cloudiness remaining, and the yield is 837 g of monobutyltin mercaptide of the formula $n-C_4H_9Sn[SCH_2CH(OCOCH_3)CH_2$—O—$COC_{8-10}H_{17-21}]_3$ in the form of a clear odourless product.

Analysis: Found: 9.35% total tin; 9.1% Sn (I). Calculated: 9.38% total tin; 8.9% Sn (I).

EXAMPLE 6

10.3 g of di-n-butyltin oxide (DBTO) is added to 30 g of mercapto diester of example 2 having a mercapto content of 9.2%, and the mixture is heated at about 80° C. with stirring. The reaction water forming is removed in vacuo. The DBTO goes into solution except for a few polymeric impurities, which are removed by filtration. The yield is 39.5 g of dibutyltin dimercaptide of the formula $(n-C_4H_9)_2Sn[SCH_2CH(OCOCH_3)CH_2$—O—$COC_{8-10}H_{17-21}]_2$ in the form of a clear, viscous and completely odourless product.

Analysis: Found: 12.60% of Sn (II). Calculated: 12.55% of Sn (II).

EXAMPLE 7 (Comparative Example)

$n-C_4H_9Sn[SCH_2CH(-OCOCH_3)CH_2$—$OCOCH_3]_3$ 60.6 g of monobutyltin oxide (content: 0.245 g atom of monalkylated tin and 0.009 g atom of dialkylated tin) is heated with 146.2 g of $HSCH_2CH(OCOCH_3)CH_2OCOCH_3$ (0.761 mol) at 110° for 1 hour, and the reaction water is evaporated off in vacuo to leave a colourless viscous liquid.

EXAMPLE 8

A recipe for producing hard PVC tubes is made up as follows:

| | |
|---|---|
| S-PVC (K value 68) | 100.0 parts |
| chalk | 1.0 part |
| titanium dioxide | 1.0 part |
| calcium stearate | 0.8 part |
| paraffin wax | 0.8 part |
| monoorganotin mercaptide | 0.5–0.8%. |

There is used as a monoorganotin mercaptide according to the invention the stabiliser described in Example 5 in amounts of 0.5% (=0.046% of tin) and 0.8% (=0.074% of tin), respectively, and as comparative stabiliser is used the stabiliser produced according to Example 7 in an amount of 0.5% (=0.077% of tin). After thorough mixing of the compounds, repeated rolling tests are carried out at 200°, and specimens are taken at intervals of three minutes, and the discoloration of the specimens is measured (Yellowness Index). Reference is made to Table 1.

TABLE 1

| Stab. | | 3' | 6' | 9' | 12' | 15' | 18' | 21' | 24' | 27' |
|---|---|---|---|---|---|---|---|---|---|---|
| stab. from Example 5 | 0.5% | 13,2 | 15,5 | 21,2 | 33,9 | 54,8 | | | | |
| | 0.8% | 8,6 | 10,7 | 13,2 | 17,2 | 22,5 | 31,0 | 41,2 | 55,6 | 66,0 |
| comparative stab. from Example 7 | 0.5% | 9,8 | 12,2 | 20,4 | 41,4 | 56,7 | | | | |

Table 1 shows that in the case of employed amounts based on the same content of tin, the stabiliser produced according to the invention is clearly superior to the comparative stabiliser with regard both to the initial colour and to the long-duration stability, and even where equal weight is used, a comparable long-duration stability is obtained.

EXAMPLE 9

A hard sheet recipe is made up as follows:

| | |
|---|---|
| S-PVC (K value 64) | 100.0 parts |
| 1.3-butanediolmontanic acid ester | 0.2 part |
| glycerol monooleate | 1.0 part |
| organotin stabiliser | 0.6–1.6% |

As organotin stabilisers are used: 1% (=0.092% of tin) and 1.6% (=0.144% of tin), respectively, of the stabiliser of Example 5 according to the invention, and 0.6% (=0.092% of tin) and 1.0% (=0.153% of tin), respectively, of the comparative stabiliser described in Example 7. After thorough mixing of the compounds, a repeated rolling test at 190° is carried out, and specimens are taken at intervals of 5 minutes. The discoloration values (Yellowness Index) as a function of the load time are listed in Table 2.

TABLE 2

| Stab. | 5' | 10' | 15' | 20' | 25' | 30' | 35' | 40' | 45' | 50' | 55' | 60' |
|---|---|---|---|---|---|---|---|---|---|---|---|---|
| stab. from Ex. 5 1.0% | 4,0 | 5,6 | 9,2 | 12,8 | 25,2 | 29,9 | 50,1 | 84,3 | | | | |
| 1.6% | 3,5 | 4,4 | 7,3 | 10,7 | 20,1 | 24,7 | 31,3 | 34,1 | 38,3 | 50,9 | 77 | 96,0 |
| comparative 0.6% | 4,6 | 10,5 | 27,9 | 53,9 | 75,7 | 85,1 | | | | | | |
| stab. from Ex. 7 1.0% | 4,0 | 6,6 | 11,9 | 29,4 | 49,2 | 65,7 | 79,3 | | | | | |

It is clear from Table 2 that the stabiliser according to the invention, on the basis of an equal tin content, is clearly superior to the comparative stabiliser, and even more clearly superior where the amounts of stabiliser used are equal.

EXAMPLE 10 n-C$_4$H$_9$Sn[SCH$_2$CH(OCOCH$_2$COCH$_3$)CH$_2$—O—COC$_{8-10}$H$_{17-21}$]$_3$ 7.31 g of mono-n-butyltin oxide (content: 0.0295 gram atom of monoalkylated tin and 0.01303 gram atom of dialkylated tin) is reacted for one hour with 33.70 g of

HSCH$_2$CH(OCOCH$_2$COCH$_3$)CH$_2$—O—COC$_{8-10}$H$_{17-21}$ (94.7%=0.0922 mol) at 110°, and the reaction water is removed in a water-jet vacuum. The result is an odourless viscous liquid (tin calculated: 9.2%, found: 9.3%).

What is claimed is:

1. An organotin compound of the formula I $$(C_1\text{–}C_{12}\text{–Alkyl})_n\text{–Sn–}(S\text{–}CH_2\underset{\underset{OR}{|}}{CH}CH_2\text{–}\underset{\underset{O}{\|}}{O}CC_{8-10}H_{17-21})_{4-n} \quad (I)$$

wherein n is 1 or 2, and R is a C$_1$–C$_{18}$-acyl group.

2. A compound of the formula I according to claim 1, wherein n is 1 or 2, and R is C$_1$–C$_{18}$-alkanoyl or acetoacetyl.

3. A compound of the formula I according to claim 1, wherein n is 1, and R is acetyl, propionyl or acetoacetyl.

4. A compound of the formula I according to claim 1, wherein the alkyl bound to the tin is methyl, n-butyl or n-octyl, n is 1, and R is acetyl, propionyl or acetoacetyl.

5. A compound according to claim 1 of the formula n-C$_8$H$_{17}$Sn[SCH$_2$CH(OCOCH$_3$)CH$_2$—O—COC$_{10}$H$_{21}$]$_3$.

6. A chlorine-containing polymer stabilised with an effective stabilizing amount of a compound according to any one of claims 1–5 inclusive.

7. A method for stabilizing halogen-containing polymers against degradation resulting from the action of heat or light which comprises incorporating in said polymer an effective stabilizing amount of a compound according to any one of claims 1–5.

* * * * *